(12) United States Patent
Fuderer et al.

(10) Patent No.: US 11,852,708 B2
(45) Date of Patent: Dec. 26, 2023

(54) RECONSTRUCTION OF SPIRAL K-SPACE SAMPLED MAGNETIC RESONANCE IMAGES

(71) Applicant: KONINKLIJKE PHILIPS N.V., Eindhoven (NL)

(72) Inventors: Miha Fuderer, Best (NL); Elwin De Weerdt, Tilburg (NL)

(73) Assignee: Koninklijke Philips N.V., Eindhoven (NL)

( * ) Notice: Subject to any disclaimer, the term of this patent is extended or adjusted under 35 U.S.C. 154(b) by 93 days.

(21) Appl. No.: 17/617,957

(22) PCT Filed: Jun. 11, 2020

(86) PCT No.: PCT/EP2020/066239
§ 371 (c)(1),
(2) Date: Dec. 10, 2021

(87) PCT Pub. No.: WO2020/249696
PCT Pub. Date: Dec. 17, 2020

(65) Prior Publication Data
US 2022/0244335 A1    Aug. 4, 2022

(30) Foreign Application Priority Data
Jun. 13, 2019  (EP) .................... 19179993

(51) Int. Cl.
*G01R 33/56* (2006.01)
*A61B 5/0537* (2021.01)
(Continued)

(52) U.S. Cl.
CPC ........ *G01R 33/5608* (2013.01); *A61B 5/0537* (2013.01); *G01R 33/4818* (2013.01); *G06T 5/006* (2013.01); *G06T 2207/10088* (2013.01)

(58) Field of Classification Search
CPC ........... G01R 33/4818; G01R 33/5608; A61B 5/0537; G06T 5/006; G06T 2207/10088
See application file for complete search history.

(56) References Cited

U.S. PATENT DOCUMENTS 10,107,882 B2 * 10/2018 de Weerdt .......... G01R 33/5607
10,646,165 B2 *  5/2020 Krishnaswamy ...... A61B 5/055
(Continued)

OTHER PUBLICATIONS

Fang et al "Multiscale Coherence Regularization Reconstruction Using a Nonlocal Operator for fast Variable-Density Spiral Imaging" Magnetic Reson in Med. 34 p. 964-973 (2016).
(Continued)

*Primary Examiner* — Gregory H Curran

(57) ABSTRACT

Disclosed herein is a medical system (100, 300, 500) comprising: a memory (110) storing machine executable instructions (120) and a processor (104). Execution of the machine executable instructions causes the processor to: receive (200) magnetic resonance imaging data (122), wherein the magnetic resonance imaging data has a spiral k-space sampling pattern; reconstruct (202) at least one preliminary magnetic resonance image (124) from the magnetic resonance imaging data; construct (204) a first set of equations comprising (130) each of the at least one preliminary magnetic resonance image being equal to an image transformation of at least one clinical image, wherein the image transformation makes use of a first spatially dependent kernel for each of the at least one clinical image (126, 126', 126"); construct (206) a second set of equations (134) comprising at least one regularization matrix (132, 132', 132") times the at least one clinical image; and numerically (208) solve the first set of equations and the second set of equations simultaneously for the at least one clinical image.

15 Claims, 7 Drawing Sheets

(51) Int. Cl.
    *G01R 33/48*     (2006.01)
    *G06T 5/00*     (2006.01)

(56) References Cited

U.S. PATENT DOCUMENTS

| | | |
|---|---|---|
| 2005/0074152 A1 | 4/2005 | Lewin et al. |
| 2008/0021303 A1 | 1/2008 | Krueger |
| 2011/0267054 A1* | 11/2011 | He .................. A61B 5/055 |
| | | 324/309 |
| 2014/0152304 A1 | 6/2014 | Fielden et al. |

OTHER PUBLICATIONS

Truong et al "Application of k-space Energy Spectrum Analysis for Inherent and Dynamic Bo Mapping and Deblurring in Spiral Imaging" Magnetic Reson in Med. 64 p. 1121-1127 (2010).
International Search Report and Written Opinion from PCT/EP2020/066239 dated Dec. 17, 2020.
Lustig et al "Spirit: Iterative Self-Consistent Parallel Imaging Reconstruction from Arbitrary k-space" Magnetic Reson in Med. Jun. 1, 2010.
Wang et al "Joint Water-fat Separation and Deblurring for Spiral Imaging" Magnetic Reson in Med. vol. 79, No. 6 p. 3218-3228 (Oct. 5, 2017).
Delattre et al "Spiral Demystified" Magnetic Resonance Imaging, vol. 28, No. 6 Jul. 1, 2010 p. 862-881.

\* cited by examiner

RECONSTRUCTION OF SPIRAL K-SPACE SAMPLED MAGNETIC RESONANCE IMAGES

CROSS REFERENCE TO RELATED APPLICATIONS

This application is a U.S. national phase application of International Application No. PCT/EP2020/066239 filed on Jun. 11, 2020, which claims the benefit of EP Application Serial No. 19179993.1 filed on Jun. 13, 2019 and is incorporated herein by reference.

FIELD OF THE INVENTION

The invention relates to Magnetic Resonance Imaging, in particular to the reconstruction of magnetic resonance images from spirally sampled k-space data.

BACKGROUND OF THE INVENTION

A large static magnetic field is used by Magnetic Resonance Imaging (MRI) scanners to align the nuclear spins of atoms as part of the procedure for producing images within the body of a patient. This large static magnetic field is referred to as the $B_0$ field or the main magnetic field. Various quantities or properties of the subject can be measured spatially using MRI. Images are reconstructed from magnetic resonance imaging data that is sampled in k-space. The k-space data may be acquired using a variety of different sampling patterns. One example is the sampling of k-space data using a spiral sampling pattern. K-space sampling patters may be vulnerable to spatial and temporal variations of the static magnetic field, which may result in image artefacts.

Truong et. al., "Application of k-Space Energy Spectrum Analysis for Inherent and Dynamic B0 Mapping and Deblurring in Spiral Imaging," Mag. Res. Med. 64:1121-1127, 2010 discloses an off-resonance correction method to counteract artefacts caused by variation in the $B_0$ field. A k-space energy spectrum analysis algorithm is used to generate a $B_0$ map from the k-space data at each time point. A simulated phase evolution rewinding algorithm is then used with a residual deblurring algorithm to correct for the blurring caused by both spatial and temporal $B_0$.

Dixon methods of magnetic resonance imaging include a family of techniques for producing separate water and lipid (fat) images. The various Dixon techniques such as, but not limited to, two-point Dixon Method, three-point Dixon method, four-point Dixon method, and six-point Dixon Method are collectively referred to herein as Dixon techniques or methods. There are typically multiple solutions when reconstructing the water and fat images. It is possible to inadvertently switch voxels between the water and fat images; this is referred to a water-fat swap herein.

SUMMARY OF THE INVENTION

The invention provides for a medical system, a method, and a computer program product in the independent claims. Embodiments are given in the dependent claims.

Embodiments may provide for an improved method of removing artefacts due to the use of a spiral k-space sampling pattern. This may be achieved by calculating the clinical images numerically from measured preliminary magnetic resonance images using a first set of equations. To remove the artefacts additional regularization equations (second set of equations) are included in the numerical solver.

In contrast to the known SpirIT reconstruction, the present invention makes use of an off-diagonal regularisation matrix defined in image space. The known SPIRiT method involves a regularisation based on consistency between synthesised k-space data that are back projected from the reconstructed image and the actually sampled k-space data. The regularisation matrix is associated with a kernel in image space that has limited support in that it extends over a finite number of more than one pixel. The matrix-multiplication by the regularisation matrix implements a convolution in image space by the kernel. The regularisation involves convolution with a kernel whereby the pattern (or contents) of the kernel vary from location to location" or as "multiplication with a matrix where the pattern of the row varies from row to row". These weights depend on the magnetic field spatial variations that were present during the acquisition (this includes then the main magnetic field, susceptibility, and eddy currents etc.).

An insight of the invention is that image artefacts may be reduced by considering an artefact preliminary image as a transformed version of an ideal high image quality corresponding clinical image. The artefact preliminary image may be reconstructed by simple inverse Fourier transform of sampled k-space data. Artefacts may arise in the artefacted preliminary image caused by the particular sampling pattern, such as e.g. spiral sampling trajectories, in k-space, i.e.

$$K_T = FT(I_b).$$

where $K_T$ is the-space data set sampled from k-space for echo time T, FT denotes the Fourier transform and may also account for different grids in k-space and image space, respectively. and $I_b$ is the artefact preliminary image, containing image artefacts due to the particular k-space sampling pattern. The artefact preliminary image $I_b$ is related to an (as yet not known) clinical image I of diagnostic image quality, by an image transformation represented by a transformation matrix C, i.e.

$$I_b = CI$$

The transformation matrix C represent the deviation between the applied spatial encoding of the acquired MR-data and the actual encoding. In particular the transformation matrix C represents how the actual spatial encoding differs from the spatial encoding applied by applied gradient encoding gradient magnetic fields. Thus the transformation matrix C represents inadvertent spatial encodings due to e.g. spatial inhomogeneities of the main magnetic field, gradient delays and deviations. The transformation matrix C may be based on a priori knowledge of the spatial distribution of inhomogeneities of the main magnetic field, e.g. in the form of an a priori estimated $B_0$-map. From this matrix equation the clinical image may be resolved using a regularisation approach in image space:

$$\begin{bmatrix} I_b \\ 0 \end{bmatrix} = \begin{bmatrix} C \\ Q \end{bmatrix} I.$$

where Q is a regularisation matrix. According to the invention Q is a non diagonal matrix which suppresses strong local signal variations, i.e. suppresses high spatial frequency components from the solution for the clinical image I. The regularisation may impose pre-set (e.g. zero) values on pixels of the image to be reconstructed where there is a high degree of uncertainty on the main magnetic field inhomogeneity. For example, in zones outside to body of the patient to be examined, the information on the main magnetic field distribution is very uncertain. The regularisation may favour zero pixel-values on these zones. The regularisation matrix is associated with a kernel in image space that has limited support in that it extends over a finite number of more than one pixel. The matrix-multiplication by the regularisation matrix implements a convolution in image space by the kernel. This type of regularisation suppresses high-spatial frequencies in the reconstructed image. The use of a spatially varying regularisation kernel may also account for local differences in the spatial inhomogeneities the main magnetic field. The spatial size (limited support in image space) determines the cut-off of the low-pass frequency band imposed by this regularisation matrix. Good results are achieved with a kernel having support of 3 to 7 voxels; in general the kernel has a support that is at least an order of magnitude more narrow than the matrix size of the image.

The artefacts may e.g. be ringing artefacts or blurring which are caused by a spiral sampling pattern in k-space. The non-diagonally of the regularisation matrix imposes that the regularisation term is affected by neighbouring voxels.

The present invention may be implemented in combination with parallel imaging. Parallel imaging involves undersampling of k-space in combination with unfolding in image space based on the receiver antennae's spatial coil sensitivity profiles. The unfolding may be included in the Fourier transforming the acquired MR-data to yield the artefact image from which (most of) the folding artefacts have been removed. Alternatively the unfolding may be included in the recovering the diagnostic image (i.e. as part of the deblurring and from which artefacts have been removed) from the preliminary artefacted containing folding artefacts.

This technique can be applied in several ways. In Dixon magnetic resonance imaging, prior knowledge such as provided by a water and/or fat mask can be used to reduce the number of artefacts. In another application the use of a regularization matrix with off diagonal terms (i.e. a non-diagonal regularization matrix) can be used to reduce or eliminate image artefacts such as blurring or ringing effects. The use of a non-diagonal regularization matrix may also be applied to Dixon imaging.

In one aspect the invention provides for a medical system that comprises a memory which stores machine-executable instructions. The medical system further comprises a processor. Execution of the machine-executable instructions causes the processor to receive magnetic resonance imaging data. The magnetic resonance imaging data has a spiral k-space sampling pattern. Execution of the machine-executable instructions further causes the processor to reconstruct at least one preliminary magnetic resonance image from the magnetic resonance imaging data.

Execution of the machine-executable instructions further cause the processor to construct a first set of equations comprising each of the at least one of preliminary magnetic resonance images being equal to an image transformation of at least one clinical image. The image transformation makes use of a first spatially dependent kernel for each of the at least one clinical image. The first spatially dependent kernel may for example be used to make a convolution of all of the clinical images to arrive at the individual preliminary magnetic resonance images. Execution of the machine-executable instructions further causes the processor to construct a second set of equations comprising at least one regularization matrix times the at least one clinical image.

For example, the at least one regularization matrix times the at least one clinical image could be set to be equal to zero to provide regularization equations. Execution of the machine-executable instructions further causes the processor to numerically solve the first set of equations and the second set of equations simultaneously for the at least one clinical image. The numerical solution of the at least one clinical image may be considered to be an inverse problem. The at least one preliminary magnetic resonance image are the images that are measured or determined experimentally and then the at least one clinical image is determined numerically from these preliminary magnetic resonance image or images.

A medical system as used herein may in some examples encompass a computer system which is programmed for performing the image processing and magnetic resonance imaging construction techniques that are performed by the processor. This functionality may for example be integrated into different types of systems. It may be available remotely via a cloud system. It may for example be a workstation that is for example being used in a radiology or other medical centre. The functionality may also be incorporated into a medical imaging scanner such as a magnetic resonance imaging system.

The embodiment may be beneficial because it may provide for a means of removing artefacts from magnetic resonance images. In particular it may be efficient in removing artefacts from images that have a spiral k-space sampling pattern.

In another embodiment the simultaneous solution of the first set of equations and the second set of equations results in a removal of artefacts caused by the spiral k-space sampling pattern from the at least one clinical image.

In another embodiment each of the at least one clinical image represents a concentration of one type of a molecular species. This embodiment may be beneficial because it may be useful in various types of magnetic resonance imaging protocols where various types of material such as fat, water, or spinal fluid are suppressed.

In another embodiment the at least one clinical image is a Dixon water image and a fat image. In this case there are only two clinical images. The image transformation comprises a convolution of the Dixon water image and the Dixon fat image using the first spatially dependent kernel for each of the at least one clinical image. This embodiment may be beneficial because it may provide for a means of providing for improved Dixon water images and Dixon fat images.

In another embodiment the at least one regularization matrix comprises a water regularization matrix and a fat regularization matrix. That is to say the Dixon water image has its own water regularization matrix and the Dixon fat image has its own fat regularization matrix. The construction of the second set of equations is performed by multiplying the water regularization matrix times a matrix representation of the Dixon water image. The construction of the second set of equations is further performed by multiplying the fat regularization matrix times a matrix representation of the Dixon fat image.

In one example the equations may be constructed such that zero is set equal to the water regularization matrix times the matrix representation of the Dixon water image and again, zero is set equal to the multiple of the fat regularization matrix times the matrix representation of the Dixon fat image.

In another embodiment execution of the instructions further causes the processor to perform the multiplication of the water regularization matrix times a water mask before constructing the second set of equations. A water mask as used herein is a mask or image which is used to indicate a known location of water or water voxels within the magnetic resonance image. For example, a low resolution or other information may be used to provide this information a fortiori. This may improve water and fat separation during the reconstruction.

Execution of the machine-executable instructions further causes the processor to multiply the fat regularization matrix times a fat mask before constructing the second set of equations. The fat mask is a mask which is used to indicate either a presence or even a concentration of fat within various voxels. This information may be known before the reconstruction for example from lower resolution scans or other information.

The water mask and the fat mask may be considered to be combining prior knowledge of the location or concentration of fat and water within the subject to improve the reconstruction of the Dixon water image and the Dixon fat image.

For example, the water and fat masks may be used to indicate a concentration or partial volume of water or fat within a particular voxel. In some instances, this information is obtained through separate imaging or information. In other examples these masks could for example be from a prior iteration of trying to construct the Dixon water image and the Dixon fat image.

In another embodiment the water mask comprises a per voxel water value inversely proportional to a water content of each voxel in the Dixon water image. The fat mask comprises a fat value inversely proportional to a fat content of each voxel in the Dixon fat image. By making these values inversely proportional as there is less fat or water within a particular voxel, it causes the regularization terms to drive the fat or water content in the resulting Dixon water image or Dixon fat image to lower values. This may provide for an effective means of improving the numerical determination of the Dixon water image and the Dixon fat image.

In another embodiment the at least one regularization matrix is a non-diagonal matrix. The use of a non-diagonal matrix as a regularization matrix may have the advantage that the regularization term is affected by neighbouring voxels. This may for example be very useful in reducing artefacts such as a ringing effect.

In another embodiment execution of the machine-executable instructions further causes the processor to construct the at least one regularization matrix using a second spatially dependent kernel.

In another embodiment the second spatially dependent kernel is a Gaussian curvature kernel times a spatially dependent factor.

In another embodiment the second spatially dependent kernel is a mean curvature kernel times the spatially dependent factor.

In another embodiment the second spatially dependent kernel is a Laplacian kernel times the spatially dependent factor.

In another embodiment the second spatially dependent kernel is a second derivative kernel times the spatially dependent factor.

In another embodiment the second spatially dependent kernel is a low pass spatial filter kernel. The kernels listed above can be designed so that they are more sensitive to high spatial frequencies instead of low spatial frequencies. As a practical matter the low spatial frequencies are limited by the size of the kernel. For example if the second spatially dependent kernel is a second derivative kernel and uses a 3 element kernel than the spatial sensitivity is limited to the adjacent kernels.

In another embodiment the spatially dependent factor is any one of the following: a spatially dependent signal-to-noise estimate, a spatially dependent estimate of a B0 magnetic field gradient, a spatially dependent estimate of a $B_0$ magnetic field error, and combinations thereof. This embodiment may be beneficial because the use of the noise estimate, the B0 magnetic field gradient or the $B_0$ magnetic field error may be useful in knowing how well the image is known at this point.

In another embodiment the second spatially dependent kernel further comprises an identity term times an additional spatially dependent factor. For example, there may be additional diagonal terms such as one would find in a diagonal matrix. The diagonal matrix is typically used for regularization. This embodiment enables the use of the non-diagonal regularization at the same time as using a diagonal regularization.

In another embodiment the medical system further comprises a magnetic resonance imaging system configured for acquiring the magnetic resonance imaging data from an imaging zone. The memory further contains pulse sequence commands configured for acquiring the magnetic resonance imaging data using the spiral k-space sampling pattern. Execution of the machine-executable instructions further causes the processor to control the magnetic resonance imaging system to acquire the magnetic resonance imaging data by controlling the magnetic resonance imaging system with the pulse sequence commands.

In another embodiment the pulse sequence commands are configured to control the magnetic resonance imaging system according to a magnetic resonance imaging protocol. The magnetic resonance imaging protocol is any one of the following: a Dixon magnetic resonance imaging protocol, a two-point Dixon magnetic resonance imaging protocol, a three-point Dixon magnetic resonance imaging protocol, a four-point Dixon magnetic resonance imaging protocol, a greater than four-point Dixon magnetic resonance imaging protocol, a sensitivity-encoded parallel magnetic resonance imaging protocol, and an echo-planar imaging magnetic resonance imaging protocol. This embodiment may be beneficial because any of these imaging techniques may benefit from the invention.

In another aspect the invention provides for a computer program product comprising machine-executable instructions for execution by a processor controlling a medical system. Execution of the machine-executable instructions causes the processor to receive magnetic resonance imaging data. The magnetic resonance imaging data has a spiral k-space sampling pattern. Execution of the machine-executable instructions further causes the processor to reconstruct at least one preliminary magnetic resonance image from the magnetic resonance imaging data.

Execution of the machine-executable instructions further cause the processor to construct a first set of equations comprising each of the at least one preliminary magnetic resonance images being equal to an image transformation of at least one clinical image. The image transformation makes use of a first spatially dependent kernel for each of the at least one clinical image. Execution of the machine-executable instructions causes the processor to construct a second set of equations comprising at least one regularization matrix times the at least one clinical image. Execution of the machine-executable instructions further causes the processor to numerically solve the first set of equations and the second set of equations simultaneously for the at least one clinical image. The advantages of this have been previously discussed.

In another aspect the invention provides for a method of operating a medical system. The method comprises receiving magnetic resonance imaging data. The magnetic resonance imaging data has a spiral k-space sampling pattern. The method further comprises reconstructing at least one preliminary magnetic resonance image from the magnetic resonance imaging data. The method further comprises constructing a first set of equations comprising each of the at least one preliminary magnetic resonance image being equal to an image transformation of at least one clinical image. The image transformation makes use of a first spatially dependent kernel for each of the at least one clinical image. The method further comprises constructing a second set of equations comprising at least one regularization matrix times the at least one clinical image. The method further comprises numerically solving the first set of equations and the second set of equations simultaneously for the at least one clinical image. The method of the invention includes the steps of receive magnetic resonance imaging data ($K_T(u,v)$) (122) by sampling k-space, in particular along a spiral trajectory, Fourier transform the acquired MR-data ($K_T(u,v)$) to form a preliminary artefact (blurring, ringing) image ($I_b(m,n)$), access a pre-determined artefacting matrix (C) which transforms the diagnostic image into the blurred image and recover a diagnostic image ($I(m,n)$) through solving an optimisation problem in image space that connects the diagnostic image to the preliminary artefact image by the transformation by the matrix C to the preliminary artefact image, which optimisation involves a regularisation with which an off-diagonal regularisation matrix is associated in image space.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fibre cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analogue input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) imaging data is defined herein as being the recorded measurements of radio frequency signals emitted by atomic spins using the antenna of a Magnetic resonance apparatus during a magnetic resonance imaging scan. Magnetic resonance data is an example of medical image data. A Magnetic Resonance Imaging (MRI) image or MR image is defined herein as being the reconstructed two- or three-dimensional visualization of anatomic data contained within the magnetic resonance imaging data. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
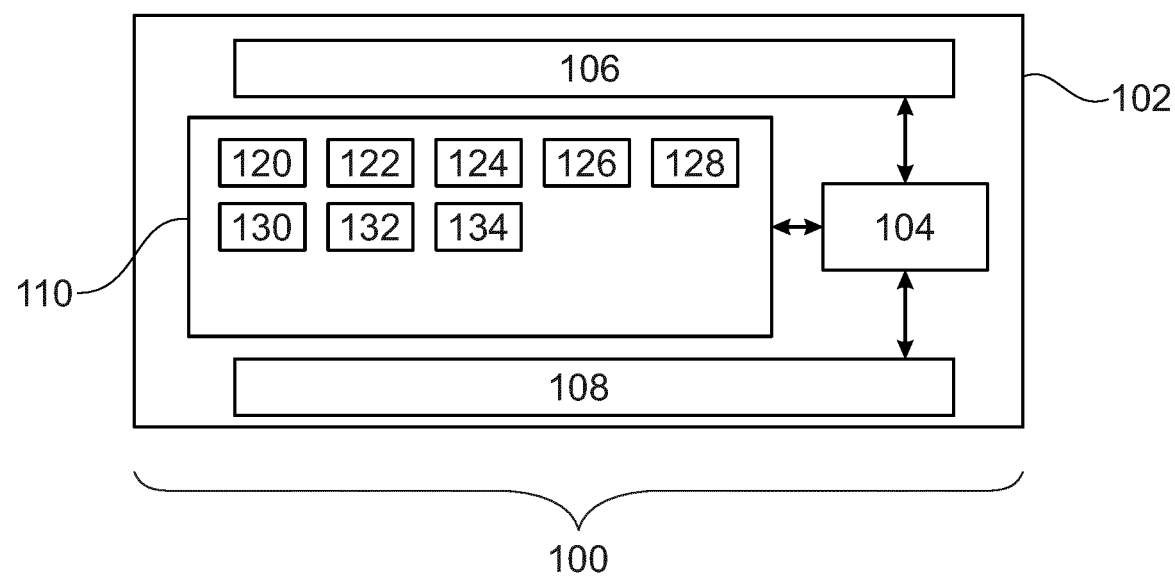
FIG. 1 illustrates an example of a medical system.

FIG. 1 illustrates an example of a medical system 100. In this example the medical system comprises a computer 102 with a processor 104. The processor is intended to represent one or more processors. The processors for example may be multiple cores. In other examples the processors 104 may be distributed between multiple computer systems and/or server units. The processor 104 is shown as being connected to an optional hardware interface 106. The hardware interface may for example be a network connection that enables the processor 104 to communicate with other computer systems and/or to communicate or control other components of the medical system 100. For example, the processor in some examples may be useful for controlling a magnetic resonance imaging system. The processor 104 is also shown as being connected to an optional user interface 108. The processor 104 is shown as being further connected to a memory 110.

The memory 110 may be any combination of memory which is accessible to the processor 104. This may include such things as main memory, cached memory, and also non-volatile memory such as flash RAM, hard drives, or other storage devices. In some examples the memory 110 may be considered to be a non-transitory computer-readable medium.

The memory stores machine-executable instructions 120. The machine-executable instructions 120 enable the processor 104 to perform various data and image manipulation operations. In some examples the machine-executable instructions 120 also enable the processor 104 to control additional components via the hardware interface 106. The memory 110 is further shown as containing magnetic resonance imaging data 122 that has a spiral k-space sampling pattern. The magnetic resonance imaging data 122 may be received in various ways. It may for example be transferred to the memory 110 from another memory device or it may for example be received from a magnetic resonance imaging system or transferred via network connection.

The memory 110 is further shown as containing at least one preliminary magnetic resonance image 124 that was reconstructed from the magnetic resonance imaging data 122. The memory 110 is further shown as containing at least one clinical image 126 that was calculated numerically from the at least one preliminary magnetic resonance image 124. The memory 110 is further shown as containing a first spatially dependent kernel 128 that was used to generate a first set of equations 130. There is at least one regularization matrix 132 also stored in the memory 110 which is used to generate a second set of equations 134 which is also shown as being stored in the memory 110. The first set of equations 130 and the second set of equations 134 are solved numerically to obtain the at least one clinical image 126.

Figure 2:
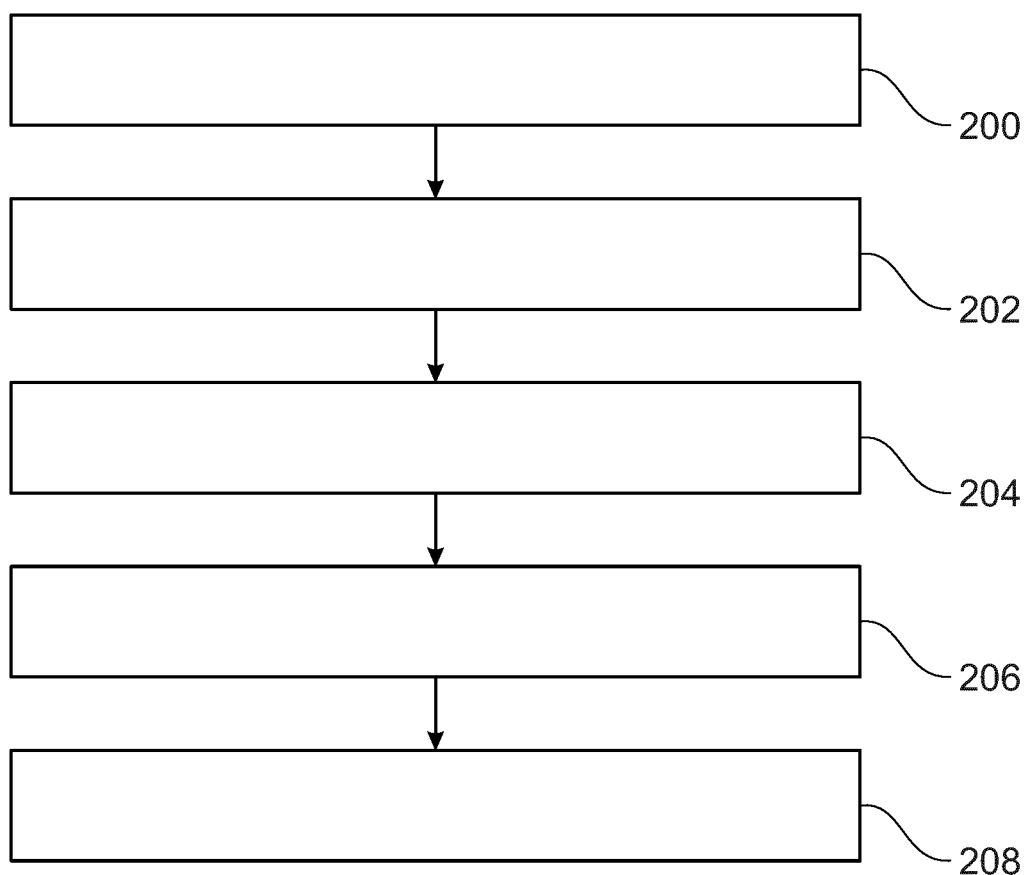
FIG. 2 shows a flow chart which illustrates a method of operating the medical system of FIG. 1.

FIG. 2 shows a flowchart which illustrates a method of operating the medical system 100 of FIG. 1. First in step 200 the magnetic resonance imaging data 122 is received. The magnetic resonance imaging data has a spiral k-space sampling pattern. Next in step 202 the at least one preliminary magnetic resonance image 124 is reconstructed from the magnetic resonance imaging data 122. Then in step 204 the first set of equations 130 is constructed. The first set of equations comprise each of the at least one preliminary magnetic resonance image 124 being equal to an image transformation of at least one clinical image 126. The image transformation makes use of a first spatially dependent kernel 128 for each of the at least one clinical image 126. Next in step 206 a second set of equations 134 is constructed. The second set of equations comprise at least one regularization matrix 132 times the at least one clinical image 126.

In some examples the regularization matrix 132 may be the same for each clinical image 126. In other examples there may be an individual regularization matrix for each clinical image 126. Finally, in step 208 the first set of equations 130 and the second set of equations 134 are solved simultaneously to numerically obtain the at least one clinical image 126.

A possible modification of the technique illustrated in FIG. 2 is that the regularization matrix 132 is constructed using a non-diagonal matrix. The construction of the second set of equations 134 would then be performed using the non-diagonal regularization matrix. This modification could for example be achieved by using a second spatially dependent kernel to construct the regularization matrix. The kernel may be used for measuring for example the local curvature and/or derivative within a particular location. This may be very useful for removing spatially dependent or repeating artefacts. For example, the second spatially dependent kernel could be a Gaussian curvature kernel times a spatially dependent factor, a mean curvature kernel times spatially dependent factor, a Laplacian kernel times a spatially dependent factor, and a second derivative kernel time the spatially dependent factor.

The spatially dependent factor may be useful in calculating how well the image is known at a particular location. For example, the spatially dependent factor could be a spatially dependent signal-to-noise estimate, a spatially dependent estimate of a $B_0$ magnetic field gradient, and a spatially dependent estimate of the $B_0$ magnetic field error.

Figure 3:
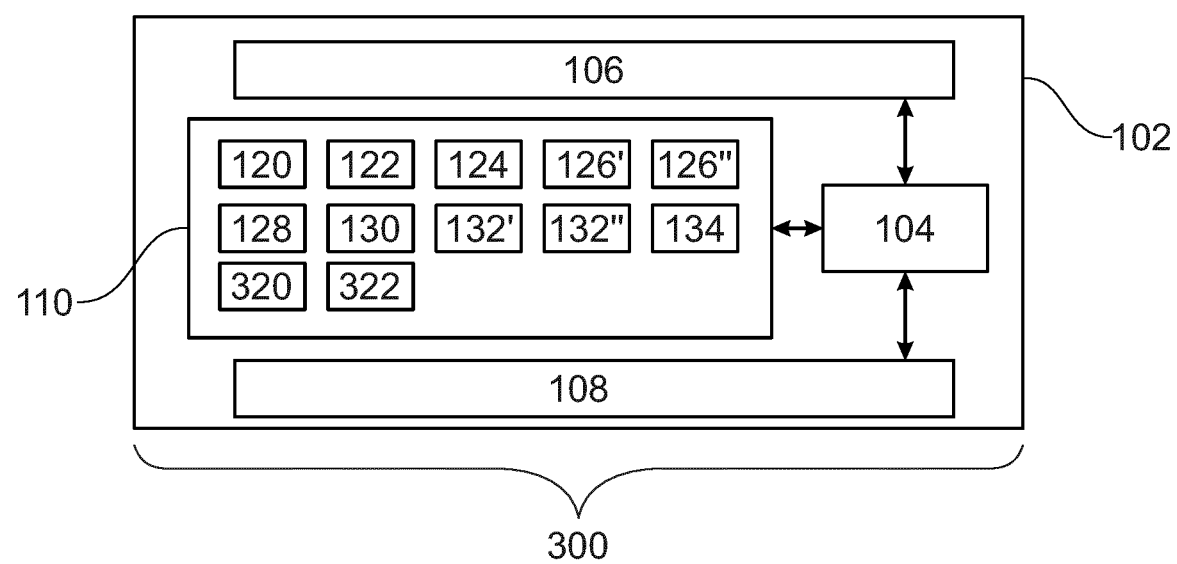
FIG. 3 illustrates an example of a medical system.

FIG. 3 illustrates a further example of a medical system 300. The medical system 300 illustrated in FIG. 3 is similar to the medical system 100 illustrated in FIG. 1. In FIG. 3 the medical system 300 has been specifically constructed or programmed to reconstruct images according to a Dixon magnetic resonance imaging protocol. The at least one clinical image 126 in this example is a Dixon water image 126' and a Dixon fat image 126". The at least one regularization matrix 132 is a separate water regularization matrix 132' for the Dixon water image 126' and a fat regularization matrix 132" for the Dixon fat image 126". The memory 110 is further shown as containing a water mask 320 and a fat mask 322.

The water mask 320 is used to identify the location or partial volume of water in individual voxels of the Dixon water image 126'. The fat mask 122 is used to identify the location of fat or partial volume of fat within voxels of the Dixon fat image 126". The water mask 320 and the fat mask 322 could be obtained in different ways. For example, they could be obtained using a lower resolution scan. In some instances, previous magnetic resonance imaging images may be segmented and this information may be used for constructing a realistic water mask 320 and/or fat mask 322.

In this example the first set of equations 130 is a convolution of the Dixon water image 126' and a Dixon fat image 126" being equal to each of the at least one preliminary magnetic resonance image 124.

In this example the construction of the second set of equations is performed by multiplying the water regularization matrix times a matrix regularization of the Dixon water image 126'. This for example may be set equal zero or a constant. The second set of equations is further constructed by multiplying the fat regularization matrix 132" times the Dixon fat image 126". This again may for example be set equal to zero or a constant.

To use the water mask 320 and the fat mask 322 the water mask 322 is multiplied by the water regularization matrix 132' and the fat mask 322 is multiplied by the fat regularization matrix 132". For example, the water mask 320 may have an element for each of the water regularization matrix 132'. Likewise, the fat mask 322 may have an element for each of the fat regularization matrix 132". In this example the multiplication would then be the multiplication of corresponding elements.

Figure 4:
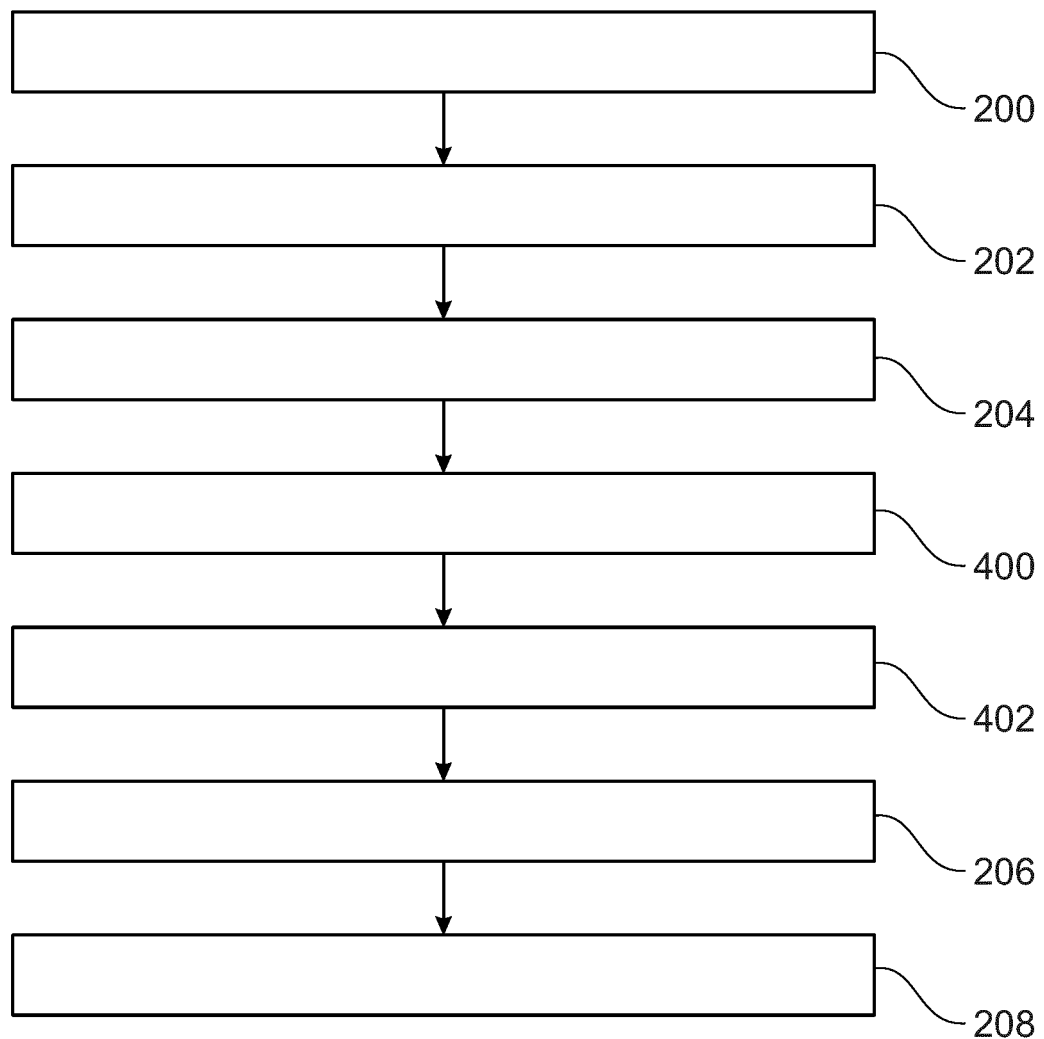
FIG. 4 shows a flow chart which illustrates a method of operating the medical system of FIG. 3.

FIG. 4 shows a flowchart which illustrates a method of operating the medical system 300 of FIG. 3. In this method steps 200, 202, and 204 are performed in an analogous way using the medical system 300 of FIG. 3. Next in step 400 the water regularization matrix 132' is multiplied by the water mask 320 before constructing the second set of equations. Next in step 402 the fat regularization matrix 132" is multiplied times the fat mask 322 before constructing the second set of equations. After this the method then performs steps 206 and 208 which are analogous to steps 206 and 208 in the method of FIG. 2.

Figure 5:
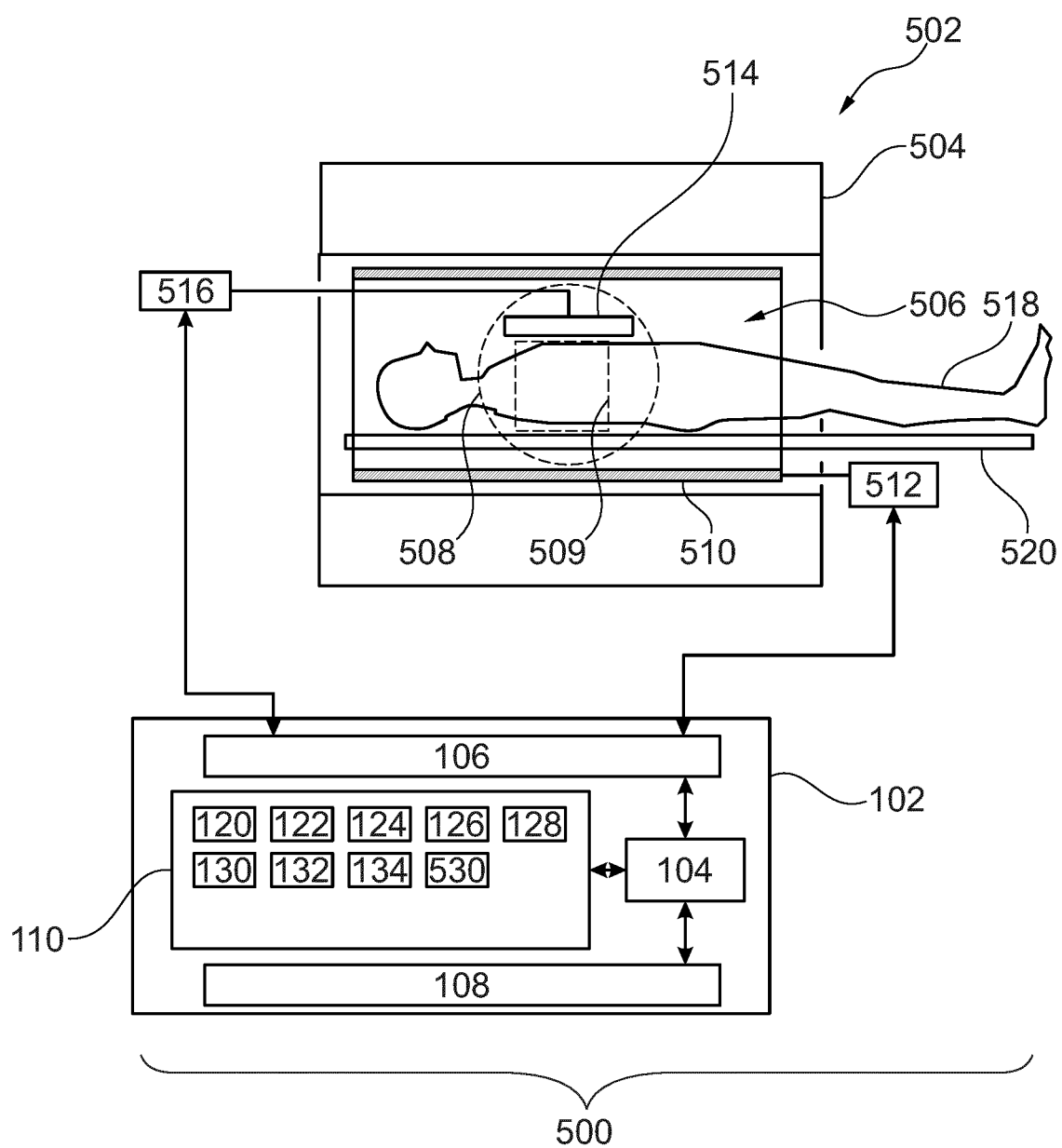
FIG. 5 illustrates an example of a medical system.

FIG. 5 illustrates a further example of a medical system 500. The medical system 500 in FIG. 5 is similar to the medical system 100 in FIG. 1 except that the medical system additionally comprises a magnetic resonance imaging system 502.

The magnetic resonance imaging system 502 comprises a magnet 504. The magnet 504 is a superconducting cylindrical type magnet with a bore 506 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils.

Within the bore 506 of the cylindrical magnet 504 there is an imaging zone 508 where the magnetic field is strong and uniform enough to perform magnetic resonance imaging. A field of view 509 is shown within the imaging zone 508. The magnetic resonance data that is acquired typically acquired for the field of view 509. A subject 518 is shown as being supported by a subject support 520 such that at least a portion of the subject 518 is within the imaging zone 508 and the field of view 509.

Within the bore 506 of the magnet there is also a set of magnetic field gradient coils 510 which is used for acquisition of preliminary magnetic resonance data to spatially encode magnetic spins within the imaging zone 508 of the magnet 504. The magnetic field gradient coils 510 connected to a magnetic field gradient coil power supply 512. The magnetic field gradient coils 510 are intended to be representative. Typically magnetic field gradient coils 510 contain three separate sets of coils for spatially encoding in three orthogonal spatial directions. A magnetic field gradient power supply supplies current to the magnetic field gradient coils. The current supplied to the magnetic field gradient coils 510 is controlled as a function of time and may be ramped or pulsed.

Adjacent to the imaging zone 508 is a radio-frequency coil 514 for manipulating the orientations of magnetic spins within the imaging zone 508 and for receiving radio transmissions from spins also within the imaging zone 508. The radio frequency antenna may contain multiple coil elements. The radio frequency antenna may also be referred to as a channel or antenna. The radio-frequency coil 514 is connected to a radio frequency transceiver 516. The radio-frequency coil 514 and radio frequency transceiver 516 may be replaced by separate transmit and receive coils and a separate transmitter and receiver. It is understood that the radio-frequency coil 514 and the radio frequency transceiver 516 are representative. The radio-frequency coil 514 is intended to also represent a dedicated transmit antenna and a dedicated receive antenna. Likewise the transceiver 516 may also represent a separate transmitter and receivers. The radio-frequency coil 514 may also have multiple receive/transmit elements and the radio frequency transceiver 516 may have multiple receive/transmit channels. For example if a parallel imaging technique such as SENSE is performed, the radio-frequency could 514 will have multiple coil elements.

The transceiver 516 and the gradient controller 512 are shown as being connected to the hardware interface 106 of a computer system 102. The memory 110 is further shown as containing pulse sequence commands. The pulse sequence commands 530 are commands or data which may be translated into such commands which control the magnetic resonance imaging system 502 to acquire magnetic resonance imaging data according to a Dixon magnetic resonance imaging protocol.

The memory 110 is shown as additionally comprising a set of pulse sequence commands 530. The pulse sequence commands 530 enable the processor 104 to control the magnetic resonance imaging system 502 to acquire the magnetic resonance imaging data 122 with a spiral k-space sampling pattern.

The features of the medical system 500 in FIG. 5 may also be freely combined with the features of the medical system 300 of FIG. 3. That is to say the pulse sequence commands 530 may be used to acquire the magnetic resonance imaging data 122 according to a Dixon magnetic resonance imaging protocol.

Figure 6:
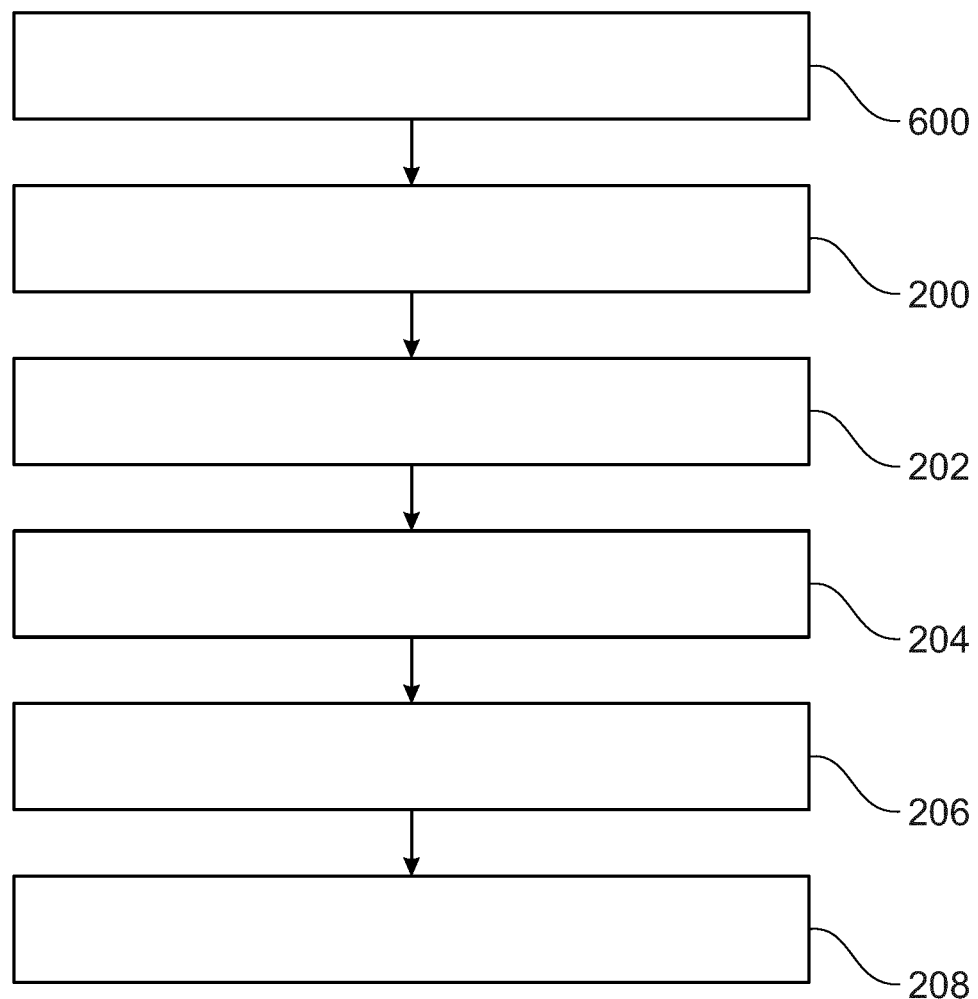
FIG. 6 shows a flow chart which illustrates a method of operating the medical system of FIG. 5.

FIG. 6 shows a method of operating the medical system 500 of FIG. 5. The method in FIG. 6 is similar to the method illustrated in FIG. 2. The method in FIG. 6 starts with step 600. In step 600 the processor 104 controls the magnetic resonance imaging system with the pulse sequence commands 530 to acquire the magnetic resonance imaging data 122. After step 600 the method proceeds to steps 200, 202, 204, 206, and 208 as is illustrated in FIG. 2.

In spiral scan reconstruction (of magnetic resonance imaging data with a spiral k-space sampling patter), a regularization step within the 'deblurring' step can be beneficial for image quality. Examples may implement this regularization as a high-pass filtering; that may be spatially dependent. The regularization level (or its exact shape) may depend on the gradient of the estimated field-deviation in that position.

Examples may relate to the reconstruction of spiral scans (using a spiral k-space sampling pattern). In particular, it may provide an improvement upon what is known as "deblurring" correcting for blurring that occurred due to an offset of the magnetic field (using the $B_0$ magnetic field gradient and/or error), whereby the field at that location may be assumed to be known.

Examples may have the benefit that the prevention of over-enhancement of high-spatial frequencies. Nowadays, this is prevented by "stopping to iterate the numerical solution before it gets too bad", which is a pretty inexact solution to the problem.

In some examples, the deblurring may be performed by applying a regularization (constructing 206 a second set of equations) that consists of a high-pass filtering; more specifically, the regularization may comprise of a position-dependent high-pass filtering; preferably, the regularization level (or its exact shape) depend on the gradient of the estimated field-deviation in that position.

This technique is discussed in the context of a Dixon magnetic resonance imaging technique described below:

In Dixon magnetic resonance imaging a multiplicity of spiral sampling patterns are acquired in k-space. Examples are equally viable for a single echo, but mostly two or three different echo times are acquired, so the invention is written against that situation. So one acquires spiral k-space samples with slightly different echo times $TE_1, \ldots, TE_L, \ldots TE_E$. Mostly, these will be distributed over "one water-fat cycle" (e.g. 2.3 ms for 3 T), so for three echoes, the echo times may be chosen to differ by 0.77 ms—but this is no strict prerequisite. All of these images (the preliminary magnetic resonance images 124) will, at least locally, be unshar.

A process of image reconstruction is as follows: as input the (complex) data from the three aforementioned echoes, which will be called $\tilde{I}_{b1}, \ldots, \tilde{I}_{bi}, \ldots, \tilde{I}_{bE}$. The tilde symbol (~) indicates the presence of blurring. The Fourier transform of these images (the preliminary magnetic resonance images 124) is denoted as $K_{Ti}(u,v)$. One may denote the "true" water image (Dixon water image 126'), which one does not know but would like to derive, as $I_W(m,n)$. Equivalently, the unknown fat image (Dixon fat image 126") is called $I_F(m,n)$.

The unregularized "forward model" is expressed as:

$$K_{Ti}(u, v) = \sum_{m,n} I_W(m, n) \cdot \exp\left(\frac{j2\pi(mu + nv)}{N}\right) \cdot \exp(j\gamma\Delta B_0(m, n) \cdot (TE_i + t(u, v))) + \sum_{m,n} I_F(m, n) \exp\left(\frac{j2\pi(mu + nv)}{N}\right) \cdot \exp(j\gamma\Delta B_0(m, n) \cdot (TE_i + t(u, v))) \cdot \exp(j\Delta f_F \cdot (TE_i + t(u, v)))$$

Read $K_{Ti}(u,v)$ as "the k-space signal observed at echo i at k-space positions (u,v)"; read $I_W(m,n)$ as "the true water-proton concentration at spatial positions (m,n)" and similarly $I_F(m,n)$ for "fat"; read $\Delta B_0(m,n)$ as "the deviation of the field at spatial position (m,n) relative to the nominal magnetic field" (which information is provided from 'outside', e.g. a field-map generated from a pre-scan); read t(u,v) as "the time at which the k-space sample (u,v) is acquired, relative to the first sample of the spiral-readout" (t(u,v) is assumed to have the same shape for all echoes); read $TE_i$ as "the difference of the time-point of the first sample of echo i, relative to the spin-echo time point of the sequence"; and read $\Delta f_F$ as "the difference in frequency between fat and water-protons" (a somewhat simplified formula, since fat actually has more than one spectral component, but one dominates).

If one considers the Fourier-transform of $K_{Ti}(u,v)$, called $\tilde{I}_{bi}$, one could recognize that this can be written as a convolution of I with a position-dependent kernel (corresponding to exp(jγΔB_0(m,n)·(TE_i+t(u,v)))) and a convolution of $I_F$ with another position-dependent kernel (corresponding to exp (jγΔB_0(m,n)·(TE_i+t(u,v)))exp(jΔf_F(TE_i+t(u,v))), typically known. This can also be written in matrix-notation, $$\tilde{I}_{bi} = C_{Wi}I_W + C_{Fi}I_F,$$

which can be read as follows: $I_W$ and $I_F$ are column-vectors, each element corresponding to one pixel location; $C_{Wi}$ and $C_{Fi}$ are matrices (number-of-pixels×number-of-pixels) representing the position-dependent 'blurring' kernels. In still more of a matrix notation, $$\tilde{I}_{bi} = \begin{bmatrix} C_{Wi} & C_{Fi} \end{bmatrix} \begin{bmatrix} I_W \\ I_F \end{bmatrix}.$$

Or, if all of the equations are stacked:

$$\tilde{I}_b = \begin{bmatrix} \tilde{I}_{b1} \\ \vdots \\ \tilde{I}_{bi} \\ \vdots \\ \tilde{I}_{bE} \end{bmatrix} = \begin{bmatrix} C_{W1} & C_{F1} \\ \vdots & \vdots \\ C_{Wi} & C_{Fi} \\ \vdots & \vdots \\ C_{WE} & C_{FE} \end{bmatrix} \begin{bmatrix} I_W \\ I_F \end{bmatrix}.$$

This can be written, short-hand, as $$\tilde{I}_b = C \begin{bmatrix} I_W \\ I_F \end{bmatrix}.$$

This is an example of the first set of equations 130.

The solution consists of iteratively resolving $I_W$ and $I_F$ from the knowledge of C and $\tilde{I}_b$, e.g. by using, for example, steepest descent of conjugate-gradients.

The approach above can be improved by using regularization by constructing the second set of equations 134. A regularization of the solution (construction of the second set of equations 134) may be adding by including a constraint to the equations, i.e. by extending:

$$C \begin{bmatrix} I_W \\ I_F \end{bmatrix} = \tilde{I}_b$$

Into the set of equations $$\begin{cases} C \begin{bmatrix} I_W \\ I_F \end{bmatrix} = \tilde{I}_b \\ \begin{bmatrix} Q_W & Q_F \end{bmatrix} \begin{bmatrix} I_W \\ I_F \end{bmatrix} = 0 \end{cases}$$

One may choose $Q_W$ and $Q_F$ to be identical as a simple case. $Q_W$ and $Q_F$ are water 132' and fat 132" regularization matrices respectively and are used to form the second set of equations 134.

If the Q matrices were to be diagonal, this would lead to a very plain regularization approach (linking it to more common classical jargon, the regularization matrix R corresponds to $(Q^hQ)^{-1}$, so one can write "$R^{-1/2}$" rather than "Q"). The essence here is to make Q non-diagonal, in the sense that it imposes only the high spatial frequencies of $I_W$ and $I_F$ to be zero.

Actually, each row of (e.g.) $Q_W$ indicates which combination of pixels from $I_W$ is supposed to be zero. Taking a hypothetical 1-dimensional situation to give an example, if one constructs the $7^{th}$ row of $Q_W$ to look as follows,
[0 0 0 0 0 −q/2 q −q/2 0 0 . . . ],
this actually imposes that the $2^{nd}$ order derivative of $I_W$ around the $7^{th}$ pixel should be zero. The larger the value of q, the stronger one imposes that constraint.

There is actually a rationale for such an endeavour. This stems from the following model: one wants to image an object using spiral scanning; that object also contains regions where the main-field deviation exhibits a field-gradient (which is of course unwanted, but it is present nevertheless). Whereas in regions of no field-gradient the spiral is well-behaved (plot 700 in FIG. 7 below), in the local presence of e.g. an x-gradient, the spiral 'drifts away' (plot 702 in FIG. 7 below).

Figure 7:
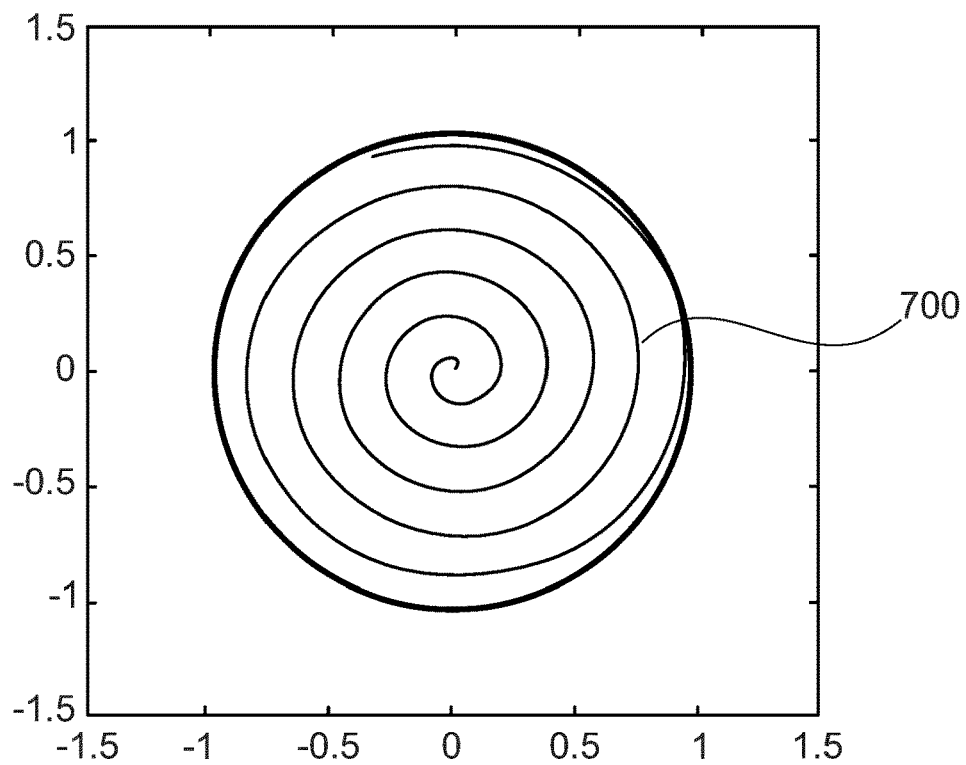
FIG. 7 illustrates examples of a spiral k-space sampling pattern.
Figure 7:
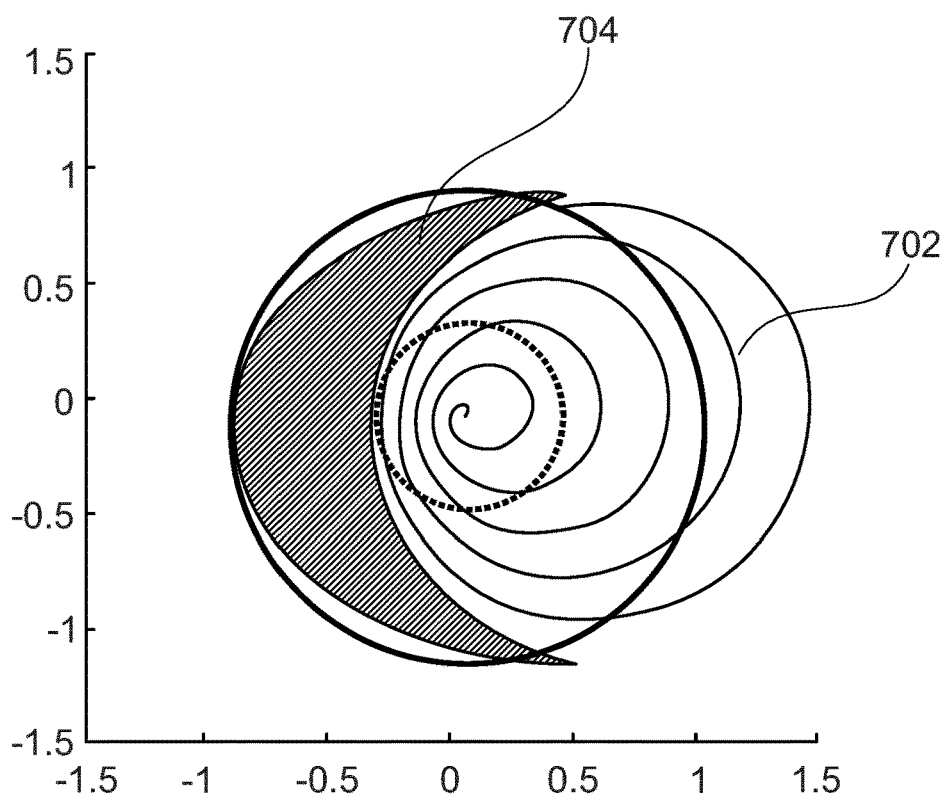

FIG. 7 illustrates several spiral k-space sampling patterns 700, 702. In the top Fig. a spiral k-space sampling pattern 700 is represented. In the lower illustration the spiral k-space sampling pattern 702 is shown as being distorted due to a high gradient of the B₀ magnetic field. The area marked 704 is intended to be sampled but is not able to be because of distortions of the sampling pattern 702.

Without appropriate regularization, the reconstruction algorithm attempts to reconstruct meaningful data corresponding to the spatial frequencies within the circle. It simply does not have enough information to meaningfully reconstruct the information corresponding to the area 704 in plot 702.

Via regularization, one can 'tell' the algorithm that the area 704 is expected to be unreliable. This can be done by an appropriate high-pass filter in that region of the matrix Q. And since one does have an estimate of the local field-gradient, one can estimate the size of the region that the spiral does reach and by that, the extent of the unreliable region. An elaborate implementation would consist of implementing each row of Q by the inverse Fourier transform of the grey-shaded area represented above.

The regularization matrices 132, 132', 132" may be constructed using kernels. This is illustrated in the examples below using a 1-dimensional "image." This simplifies the explanation and the and extension to two dimensional matrices is straightforward.

In this simplified example, Multiplying an image with a scalar a can also be seen by multiplying the vector with a diagonal matrix, i.e.:

| a | 0 | 0 | 0 | 0 | 0 |
|---|---|---|---|---|---|
| 0 | a | 0 | 0 | 0 | 0 |
| 0 | 0 | a | 0 | 0 | 0 |
| 0 | 0 | 0 | a | 0 | 0 |
| 0 | 0 | 0 | 0 | a | 0 |
| 0 | 0 | 0 | 0 | 0 | a |

A convolution with a fixed kernel (e.g. a 3-points kernel [a b c]) can also be written as a matrix multiplication, the matrix being:

| b | c | 0 | 0 | 0 | 0 |
|---|---|---|---|---|---|
| a | b | c | 0 | 0 | 0 |
| 0 | a | b | c | 0 | 0 |
| 0 | 0 | a | b | c | 0 |
| 0 | 0 | 0 | a | b | c |
| 0 | 0 | 0 | 0 | a | b |

Typically, a matrix like $C_{W1}$ (from above) could for example look approximately like this:

| 1 | 0 | 0 | 0 | 0 | 0 |
|---|---|---|---|---|---|
| 0.1 | 0.8 | 0.1 | 0 | 0 | 0 |
| 0.1 | 0.2 | 0.4 | 0.2 | 0.1 | 0 |
| 0 | −0.2 | 0.8 | −0.2 | 0.8 | −0.2 |
| 0 | 0 | −0.2 | 0.8 | −0.2 | 0.8 |
| 0 | 0 | 0 | 0 | 0.1 | 0.8 |

In this example, in the 'topmost' region, there is hardly any field error and so the blurring kernel is represented by a single peak ([0 0 0 1 0 0]); further down the 'image' (in this example the 4$^{th}$ pixel) the field substantially deviates, which causes a blurring represented by the kernel [0 0 −0.2 0.8 −0.2 0.8 −0.2 0 0].

(In practice, the kernel elements would be complex, but this is omitted here for the sake of explanation). In the same way, the regularization matrix Q can also be seen as a matrix as well as a convolution with spatially-dependent kernels.

Returning to the construction of the second set of equations, a simplified form is to fill each row of Q by a two-dimensional 2nd-derivative kernel. For example:

q/4 q/2 q/4
q/2 q q/2 and derive q by multiplying
q/4 q/2 q/4

1/(The estimate of the SNR of the end-result I at that location)

$(k_r/k_e)^2$, where $k_r$ is the nominal k-space extent (the radius of the brown circle) and $k_e$ is the radius of a circle that has been fully "seen" by the spiral scan (the dashed green circle in the right drawing). This can be calculated from the knowledge of the field gradient. E.g. for constant-angular-velocity spirals, $k_e = k_r - \gamma |\nabla B| t_a$, where $t_a$ is the sampling time of the spiral.

This can be re-written as $(1/(1-\gamma |\nabla B| t_a/k_r))^2$, or, in general one has $f(\gamma |\nabla B| t_a/k_r)$ as a factor to q. ("The higher the local gradient of the static field, the higher q, i.e. the less one trusts the high spatial frequencies".) q may be considered to be an example of the spatially dependent factor in the second spatially dependent kernel.

This can be extended by writing $f(\gamma |\nabla B| t_a/k_r, \gamma \sigma_B t_a)$, where $\sigma_B$ is the expected error one has to the knowledge of the magnetic field at that location. Preferably, this can be combined as $f(\gamma |\nabla B| t_a/k_r, \gamma \sigma_B t_a) = \sqrt{(\gamma |\nabla B| t_a/k_r)^2 + (2\pi \gamma \sigma_B t_a)^2}$, so the factor preferably becomes $1/(1-\sqrt{(\gamma |\nabla B| t_a/k_r)^2 + (2\pi \gamma \sigma_B t_a)^2})^2$.

Examples may also provide for better Dixon imaging by using prior knowledge. A benefit of some examples may be the improved problem conditioning for spiral reconstruction leading to faster convergence and improved image quality (through better water/fat separation). Both elements may be beneficial to the overall success in removing or reducing artefacts in magnetic resonance imaging that uses spiral k-space sampling.

Some examples may use species dependent regularization. In Dixon magnetic resonance imaging, one can readily obtain prior knowledge on the location of water and fat (or 'fat fraction') on lower resolution within the anatomy using a pre-scan. This may for example be performed using water masks 320 and fat masks 322. This information is known in the 'undeformed/non-blurred' domain and hence can directly be used in the regularization as described above (written slightly different below, this example combines the first and second set of equations):

$$\begin{bmatrix} \tilde{I}_b \\ 0 \end{bmatrix} = \begin{bmatrix} C \\ \begin{bmatrix} Q_W & 0 \\ 0 & Q_F \end{bmatrix} \end{bmatrix} \begin{bmatrix} I_W \\ I_F \end{bmatrix}$$

$Q_W$ is an example of a water regularization matrix and $Q_F$ is an example of a fat regularization matrix.

Although the problem is not solved using a least squares solver, the problem solution can be written as such:

$$\begin{bmatrix} I_W \\ I_F \end{bmatrix} = \left( C^H C + \begin{bmatrix} Q_W^H Q_W & 0 \\ 0 & Q_F^H Q_F \end{bmatrix} \right)^{-1} C^H \tilde{I}_b$$

Balancing of the regularization with the data 'consistency' term can be done similar to how it is done in SENSE.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical system
102 computer
104 processor
106 hardware interface
108 user interface
110 memory
120 machine executable instructions
122 magnetic resonance imaging data (spiral k-space)
124 at least one preliminary magnetic resonance image
126 at least one clinical image
126' Dixon water image
126" Dixon fat image
128 first spatially dependent kernel
130 first set of equations
132 at least one regularization matrix
132' water regularization matrix
132" fat regularization matrix
134 second set of equations
200 receive magnetic resonance imaging data
202 reconstruct at least one preliminary magnetic resonance image from the magnetic resonance imaging data
204 construct a first set of equations comprising each of the at least one preliminary magnetic resonance image being equal to an image transformation of at least one clinical image
206 construct a second set of equations comprising at least one regularization matrix times the at least one clinical image
208 numerically solve the first set of equations and the second set of equations simultaneously for the at least one clinical image
300 medical system
320 water mask
322 fat mask
400 multiply the water regularization matrix times a water mask before constructing the second set of equations
402 multiply the fat regularization matrix times a fat mask before constructing the second set of equations
500 medical system
502 magnetic resonance imaging system
504 magnet
506 bore of magnet
508 imaging zone
509 field of view
510 magnetic field gradient coils
512 magnetic field gradient coil power supply
514 radio-frequency coil
516 transceiver
518 subject
520 subject support
530 pulse sequence commands
600 control the magnetic resonance imaging system with the pulse sequence commands to acquire the magnetic resonance imaging data
700 spiral k-space sampling pattern
702 distorted spiral k-space sampling pattern
704 area inaccessible to sampling

The invention claimed is:

1. A medical system comprising:
a memory configured to store machine executable instructions;
a processor, wherein execution of the machine executable instructions causes the processor to:
receive magnetic resonance imaging data ($K_T(u,v)$) by sampling k-space, in particular along a spiral trajectory,
Fourier transform the acquired MR-data ($K_T(u,v)$) to form a preliminary artefact (blurring, ringing) image ($I_b(m, n)$),
access a pre-determined artefacting matrix (C) which transforms a diagnostic image into a blurred image and
recover the diagnostic image through solving an optimization problem in image space that connects the diagnostic image to the preliminary artefact image by a transformation by the matrix (C) to the preliminary artefact image, which optimization involves a regularization with which an off-diagonal regularization-matrix is associated in image space and involves convolution with a kernel, wherein the kernel has a support that is at least an order of magnitude more narrow than a matrix size of the diagnostic image.

2. The medical system of claim 1, wherein the off-diagonal regularization's convolution kernel's pattern varies from location to location.

3. The medical system of claim 1, wherein the off-diagonal regularization matrix has spatially varying weights that depend on the magnetic resonance imaging method's main magnetic field's spatial variation.

4. The medical system of claim 1, wherein the off-diagonal regularization matrix has limited support of 3 to 7 voxels in image space.

5. The medical system of claim 1, wherein at least one diagnostic image is a Dixon water image and a Dixon fat image, wherein the image transformation comprises a convolution of the Dixon water image and the Dixon fat image using the first spatially dependent kernel for each of the at least one clinical image.

6. The medical system of claim 5, wherein at least one regularization matrix comprises a water regularization matrix and a fat regularization matrix, and wherein the construction of the second set of equations is performed by multiplying the water regularization matrix times a matrix representation of the Dixon water image; and wherein construction of the second set of equations is further performed by multiplying the fat regularization matrix time a matrix representation of the Dixon fat image.

7. The medical system of claim 6, wherein execution of the machine executable instructions further causes the processor to perform at least one of the following:
- multiply the water regularization matrix times a water mask before constructing the second set of equations; or
- multiply the fat regularization matrix times a fat mask before constructing the second set of equations.

8. The medical system of claim 7, wherein the water mask comprises a per voxel water value inversely proportional to a water content of each voxel in the Dixon water image, and wherein the fat mask comprises a fat value inversely proportional to a fat content of each voxel in the Dixon fat image.

9. The medical system of claim 1, wherein execution of the machine executable instructions further causes the processor to construct at least one regularization matrix using a second spatially dependent kernel.

10. The medical system of claim 8, wherein the second spatially dependent kernel is any one of the following:
- a Gaussian curvature kernel times a spatially dependent factor;
- a mean curvature kernel times the spatially dependent factor;
- a Laplacian kernel times the spatially dependent factor; and
- a low pass spatial filter kernel times the spatially dependent factor;
- a second derivate kernel times the spatially dependent factor.

11. The medical system of claim 8, wherein the spatially dependent factor comprises any one of the following:
- a spatially dependent signal to noise estimate;
- a spatially dependent estimate of a $B_0$ magnetic field gradient; or
- a spatially dependent estimate of a B0 magnetic field error.

12. The medical system of claim 9, wherein the second spatially dependent kernel further comprises an identity term times an additional spatially dependent factor.

13. The medical system of claim 1, wherein the medical system further comprises a magnetic resonance imaging system configured for acquiring the magnetic resonance imaging data from an imaging zone, wherein the memory further contains pulse sequence commands configured for acquiring the magnetic resonance imaging data using the k-space spiral trajectory, wherein execution of the machine executable instructions further cause the processor to control the magnetic resonance imaging system with the pulse sequence commands to acquire the magnetic resonance imaging data.

14. The medical system of claim 13, wherein the pulse sequence commands are configured to control the magnetic resonance imaging system according to a magnetic resonance imaging protocol, wherein the magnetic resonance imaging protocol is any one of the following: a Dixon magnetic resonance imaging protocol, a two point Dixon magnetic resonance imaging protocol, a three point Dixon magnetic resonance imaging protocol, a four point Dixon magnetic resonance imaging protocol, a greater than four point Dixon magnetic resonance imaging protocol, a sensitivity-encoded parallel magnetic resonance imaging protocol, and an echo-planar imaging magnetic resonance imaging protocol.

15. A computer program product comprising machine executable instructions stored on a non-transitory computer readable medium for execution by a processor controlling a medical system, wherein execution of the machine executable instructions causes the processor to:
- receive magnetic resonance imaging data ($K_T(u,v)$) by sampling k-space, in particular along a spiral trajectory,
- Fourier transform the acquired MR-data ($K_T(u,v)$) to form a preliminary artefact (blurring, ringing) image ($I_b(m, n)$),
- access a pre-determined artefacting matrix (C) which transforms a diagnostic image into a blurred image and
- recover the diagnostic image through solving an optimization problem in image space that connects the diagnostic image to the preliminary artefact image by a transformation by the matrix (C) to the preliminary artefact image, which optimization involves a regularization with which an off-diagonal regularization matrix is associated in image space, and involves convolution with a kernel wherein the kernel has a support that is at least an order of magnitude more narrow than a matrix size of the diagnostic image.

* * * * *